(12) United States Patent
Drake et al.

(10) Patent No.: US 7,612,894 B2
(45) Date of Patent: Nov. 3, 2009

(54) FIBER LASER FOR ULTRASONIC TESTING

(75) Inventors: Thomas E. Drake, Fort Worth, TX (US); Marc Dubois, Keller, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 265 days.

(21) Appl. No.: 11/458,377

(22) Filed: Jul. 18, 2006

(65) Prior Publication Data

US 2008/0016965 A1    Jan. 24, 2008

(51) Int. Cl.
*G01B 11/14* (2006.01)
(52) U.S. Cl. .................... 356/614; 356/630
(58) Field of Classification Search ......... 356/614–624, 356/630, 432, 502; 372/30; 702/189; 73/621
See application file for complete search history.

(56) References Cited

U.S. PATENT DOCUMENTS 5,754,294 A * 5/1998 Jones et al. ................. 356/503
6,657,733 B1 * 12/2003 Drake, Jr. ................... 356/511
2004/0165620 A1 * 8/2004 Rogers et al. ................ 372/6
2005/0099634 A1 * 5/2005 Dubois et al. ............... 356/502

OTHER PUBLICATIONS

Cover Letter to Counsel (1 Page).
Statement by Inventors.
Exhibit A.
Exhibit B.

* cited by examiner

*Primary Examiner*—Michael A Lyons
*Assistant Examiner*—Tri T Ton
(74) *Attorney, Agent, or Firm*—Bracewell & Giuliani LLP

(57) ABSTRACT

Embodiments of the present invention relates to an improved laser for the optical detection of ultrasound. The primary task of this "first" detection laser is to illuminate the spot where a "second" laser is used to generate ultrasound in the part under test. The scattered light from the first laser is collected and analyzed with an interferometer to demodulate the surface vibrations caused by the return echoes of the ultrasound at the surface of the part. The improved detection laser (first laser) is constructed using a diode-pumped fiber laser to produce a high power single-frequency laser source.

18 Claims, 5 Drawing Sheets

FIBER LASER FOR ULTRASONIC TESTING

RELATED APPLICATIONS

This application incorporates by reference and claims the benefit of U.S. patent application Ser. No. 10/753,208 filed on 7 Jan. 2004 and entitled "REMOTE LASER BEAM DELIVERY SYSTEM AND METHOD FOR USE WITH A ROBOTIC POSITIONING SYSTEM FOR ULTRASONIC TESTING PURPOSES" to Thomas E. Drake.

This application incorporates by reference and claims the benefit of U.S. patent application Ser. No. 10/634,342 filed on 12 Feb. 2004 and entitled "METHOD AND APPARATUS FOR ULTRASONIC LASER TESTING" to Thomas E. Drake.

TECHNICAL FIELD OF THE INVENTION

The present invention relates generally to an apparatus and method of non-destructive evaluation of materials, and more particularly, to an apparatus and method of processing optical information to detect ultrasonic surface displacements through the use of at least one fiber laser to perform a non-destructive evaluation of a material.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must assess the structural integrity of composite materials. This assessment detects inclusions, delaminations and porosities. Conventional NDE methods are slow, labor-intensive, and costly. As a result, testing procedures adversely increase the manufacturing costs associated with composite structures.

Various methods and apparatuses have been proposed to assess the structural integrity of composite structures. One solution uses an ultrasonic source to generate ultrasonic surface displacements in a work piece which are then measured and analyzed. Often, the external source of ultrasound is a pulsed generation laser beam directed at the target. Laser light from a separate detection laser is scattered by ultrasonic surface displacements at the work piece. Collection optics then collect the scattered laser energy. The collection optics are coupled to an interferometer or other device, and data about the structural integrity of the composite structure can be obtained through analysis of the scattered laser energy. Laser ultrasound has been shown to be very effective for the inspection of parts during the manufacturing process.

However, the equipment used for laser ultrasound is custom-designed and is presently a limiting factors regarding inspection speed. Previous solid-state detection lasers used either flash-lamp pumped rod architectures or diode-pumped slab configurations to amplify a low power master oscillator laser. These configurations are generically referred to as master oscillator power amplifier (MOPA) lasers.

Inspection speed is currently limited by the pulse rate of the lasers. Flash-lamp pumped lasers can only operate at 100 Hz and the lamps typically only last 10's of millions of shots. Therefore these lasers are slow and expensive to operate. Diode-pumped slabs are much faster (400 Hz is current limit and 1 Khz may be possible) hut they use very expensive custom-manufactured diode arrays to pulse-pump the slabs and create a great amount of heat which can induce thermal distortion. Although diode array lifetimes are getting better, some have lasted 10B shots, they have historically been a concern due to both high-cost, reliability and thermal distortion. High-power pulsed-diode pumping of a crystal slab will introduce thermal distortions into the slab that ultimately limits the waveform quality of the laser beam. Wavefront distortion can limit the useful power of a laser and prevent efficient fiber optic delivery of the beam to the target. Each diode bar in the array may have a peak power of 40 W to 100 W and they must be physically close to each other in order to efficiently pump the side of the laser slab. The total number of diode bars in an array may be 50-100 (an array will pump each side of the slab, so possibly 200 diode bars may be used). Heat removal is a significant design issue for both the diode arrays and the slab.

SUMMARY OF THE INVENTION

Embodiments of the present invention are directed to systems and methods that substantially address the above identified needs and other needs as well. The embodiments of the present invention are further described in the following description and claims. Advantages and features of embodiments of the present invention may become apparent from the description, accompanying drawings and claims.

Embodiments of the present invention provide a method to detect ultrasonic surface displacements at a remote target. This involves generating a detection laser beam with a diode pumped fiber laser. The detection laser beam is directed at the surface of a remote target where ultrasonic surface displacements scatter the detection laser beam. Scattering the detection laser beam produces phase modulated light which may be collected and processed to obtain data representative of the ultrasonic surface displacements at the surface. Analyzing the information within the phase modulated light will result in the ability to analyze structures within the remote target.

Generating the detection laser beam further involves generating seed laser beam with a master oscillator. The seed laser beam can then be amplified with at least one diode pump laser amplifier. At least the master oscillator or the at least one diode pumped laser amplifier is a diode pumped fiber laser or fiber laser amplifier respectively. In other embodiments the master oscillator or at least one diode pumped laser amplifier may be a diode pumped slab laser while maintaining the limitation that at least either the master oscillator or at least one diode pumped laser amplifier is a diode pumped fiber laser or laser amplifier.

Another embodiment provides an ultrasonic surface inspection system or detection system operable to detect ultrasonic surface displacements on a remote target. This system includes an ultrasound generation system, a diode pumped detection fiber laser, collection optics, and a processor. The ultrasound generation system produces ultrasonic surface displacements at the remote target. This may be done mechanically or using a laser ultrasound generation system. The diode pumped detection fiber laser generates a detection laser beam that substantially illuminates the ultrasonic surface displacements at the remote target. Collection optics collect phase modulated light from the diode pumped detection fiber laser either reflected or scattered by the remote target. The processor may optically process the phase modulated light to produce an output signal containing data representative of the ultrasonic surface displacements at the remote target. Then the processor may process the output signal to assess the structural integrity of the remote target.

The diode pumped detection laser includes a master oscillator to generate a seed laser beam, and at least one diode pumped laser amplifier to amplify the seed laser beam. At least the master oscillator or the at least one diode pumped laser amplifier is a diode pumped fiber laser or laser amplifier. In other embodiments the diode pumped detection fiber laser may include a master oscillator, at least one diode pumped laser pre-amplifier, and at least one diode pumped laser amplifier. As previously stated at least one if not all of these is based on the diode pumped fiber laser.

In yet another embodiment the present invention provides a large area composite inspection system to measure ultrasonic surface displacements on the surface of a remote target in order to assess the structural integrity of the remote target. This large area composite inspection system may include an ultrasound generation system, a detection fiber laser, collection optics, an optical processor, and a signal processor. The ultrasound generation system produces ultrasonic displacements at the remote target. A detection fiber laser then illuminates the ultrasonic surface displacements with a detection laser beam. A scanning assembly generates relative motion between the illumination spot of the detection laser and the remote target. This may be achieved by any combination of scanning the detection laser beam by redirecting the beam, moving the detection laser beam, or moving the remote target. The collection optics collect phase modulated light from the detection laser beam reflected or scattered by the ultrasonic surface displacements at the remote target. The optical processor then processes the phase modulated light collected by the collection optics to produce an output signal. The signal processor then processes the output signal of the optical processor to obtain data representative of the ultrasonic surface displacements. This data may then be used to assess the integrity of the remote target. For example the internal structure of a composite material.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Figure 1:
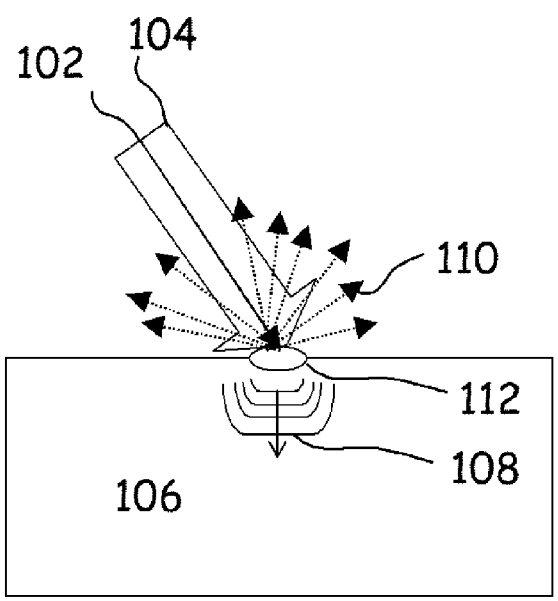
FIG. 1 illustrates the use of generation laser beam and a detection laser beam to generate and detect laser ultrasonic displacements in accordance with an embodiment of the present invention.

Preferred embodiments of the present invention are illustrated in the FIGs., like numerals being used to refer to like and corresponding parts of the various drawings.

Embodiments of the present invention provide a fiber laser for use within a laser ultrasound system. The primary task of this "first" detection laser is to illuminate the spot where a "second" laser is used to generate ultrasound in the part under test. The scattered light from the first laser is collected and analyzed with an interferometer to demodulate the surface vibrations caused by the return echoes of the ultrasound at the surface of the part. The improved detection laser (first laser) is constructed using a diode-pumped fiber laser to produce a high power single-frequency laser source.

This diode-pumped fiber laser can be constructed in many ways. One approach is to use single-frequency non-planar ring oscillator (NPRO) as a master oscillator and then subsequent amplification by one or more fiber laser amplifiers. Another approach is to construct an all-fiber single-frequency laser using a fiber-laser as the master oscillator and fiber-lasers as the amplifiers as well.

Previous solid-state detection lasers used either flash-lamp pumped rod architectures or diode-pumped slab configurations to amplify a low power master oscillator laser. These configurations are generically referred to as master oscillator power amplifier (MOPA) lasers. Flash-lamp pumped laser can operate at approximately 100 Hz and diode-pumped slab designs operate easily at 400 Hz, but could be extended to 1 kHz. A typical pulse profile would be to reach a peak power of 1000 W for of 50 us-100 us. The pulse rate of the laser is one of the factors that limits the inspection throughput of the LaserUT system.

Embodiments of the present invention provide for faster inspection rates, improved system reliability, lower operation costs and enable mobile and portable systems. Inspection speed is currently limited by the pulse rate of the lasers. Flash-lamp pumped lasers can only operate at 100 Hz and the lamps typically only last 10's of millions of shots. Therefore these lasers are slow and expensive to operate. Diode-pumped slabs are much faster (400 Hz is current limit and 1 KHz may be possible) but they use very expensive custom-manufactured diode arrays to pulse-pump the slabs. Although diode array lifetimes have improved, some have lasted 10B shots, they have historically been a concern due to both high-cost and reliability. High-power pulsed-diode pumping of a crystal slab will introduce thermal distortions into the slab that ultimately limits the waveform quality of the laser beam. Wavefront distortion can limit the useful power of a laser and prevent efficient fiber optic delivery of the beam to the target.

Each diode bar in the diode array may have a peak power of 40 W to 100 W and they must be physically close to each other in order to efficiently pump the side of the laser slab. The total number of diode bars in an array may be 50-100 (an array will pump each side of the slab, so possibly 200 diode bars may be used). Heat removal and thermal distortion becomes a significant design issue for both the diode arrays and the slab.

An all-fiber amplifier scheme uses many small continuous wave (cw) diodes to pump the doped fiber. This has several advantages. First, all of the fiber-coupled pump diodes are relatively small in power (typically only a few watts) and the loss of any one would have little impact on the total performance of the laser. Heat removal from the fiber-coupled diodes is managed separately from the gain medium (the doped fiber). These low power diodes have mean time between failure (MTBF) ratings of 100,000 hours.

Thermal management of a fiber laser/amplifier is more easily handled than within a traditional bulk crystal gain medium. The ratio of the fiber surface area (where heat is extracted) to the volume is many orders-of-magnitude larger than the surface-to-volume ratio for a slab amplifier. The fiber-laser can be operated in a single-mode (TEM00) with very little wavefront distortion ($M^2<1.2$). With a fiber laser which can now operate either in a cw mode or in a modulated (pulsed) mode, the speed limitation is not the laser speed but becomes the ultrasound propagation time and scanning capabilities. Effective scan rates could be 10 kHz or higher. Fiber lasers do not use traditional discrete or bulk optics such as mirrors or lenses. Therefore contamination issues are eliminated. A fiber laser looks like a piece of industrial electronics. Flexible architecture enables mobile and possibly portable laser ultrasonic inspection equipment designs. Overall, fiber-lasers are well suited for harsh industrial environments.

FIG. 1 depicts two incoming laser beams that generate and detect laser ultrasonic displacements. Laser beam 102 generates ultrasound while illumination laser beam 104 detects the ultrasound at a remote target 106, such as, but not limited to, a composite material under test. As shown, these lasers may be coaxially applied to remote target 106. Generation laser beam 102 causes thermo-elastic expansion 112 in target 106 that results in the formation of ultrasonic waves 108. In a different embodiment, generation laser beam causes ablation in target 106. Ultrasonic waves 108 propagate in target 106 and modulate, scatter and reflect illumination laser beam 104 to produce phase-modulated light 110 directed away from target 106 which is collected and processed to obtain information of the internal structure of remote target 106.

Figure 2:
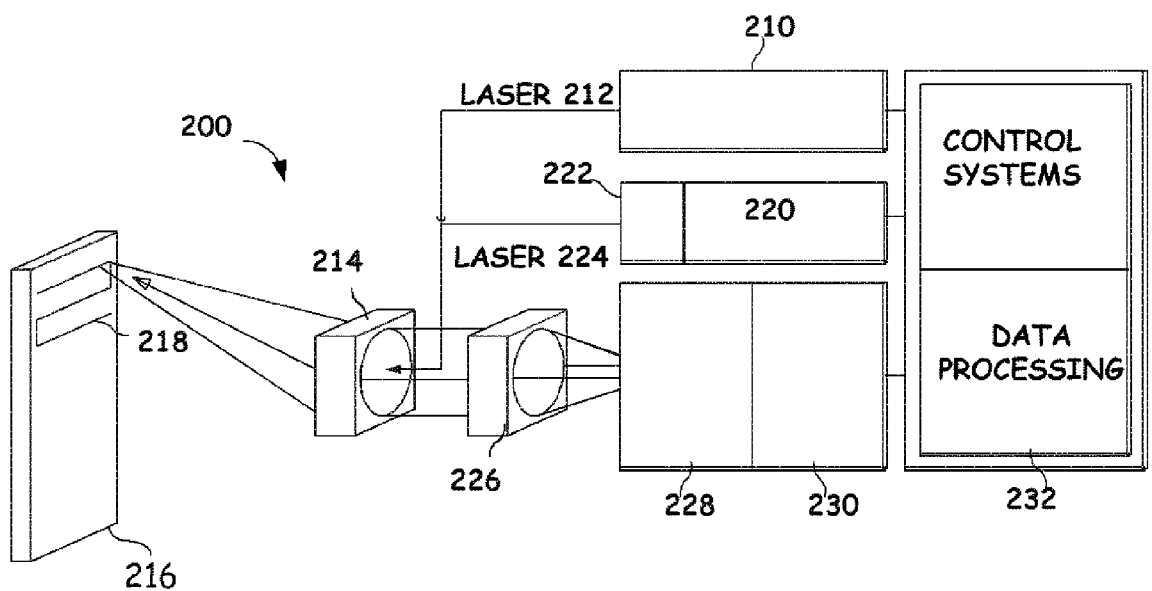
FIG. 2 provides a block diagram to show the basic components of laser ultrasound system.

FIG. 2 provides a block diagram with the basic components for performing ultrasonic laser testing. Generation laser 210 produces laser beam 212 which optical assembly 214 directs to target 216. As shown, optical assembly 214 includes a scanner or other like mechanism that moves laser beams 212 and 224 along a scan or test plan 218. Scan or test plan 218 can also be created by the movement of target 216 or by a combination of movement of target 216 and movement of laser beams 212 and 224 through assembly 214. Optical assembly 214 may include visual cameras, depth cameras, range detectors, narrowband cameras or other like optical sensors known to those having skill in the art. These optical sensors each may require calibrations prior to performing an inspection. This calibration verifies the ability of the system to integrate information gathered by various sensors. Generation laser 210 produces an ultrasonic wave 108 within target 216.

The ultrasonic wave 108 is the result of thermo-elastic expansion 112 of the composite material as the material absorbs the generation laser beam. Remote target 216 such as, but not limited to, a composite material readily absorbs generation laser beam 212 without ablating or breaking down. Higher powered generation lasers are not necessarily preferred to overcome SNR issues as these can result in ablation. In other embodiments, depending on the material being tested, some ablation may be acceptable in order to increase the SNR of the detected signal. Generation laser beam 212 has appropriate pulse duration to induce ultrasonic surface deformations. For example, a transverse-excited atmospheric (TEA) $CO_2$ laser can produce a 10.6 micron wavelength beam for a 100 nanosecond pulse. The power of the laser must be sufficient to deliver, for example, a 0.25 joule pulse to the target, which may require a 100 watt laser operating at a 400 Hz pulse repetition rate. Generation laser beam 212 is absorbed and creates heat into the target surface thereby causing thermo-elastic expansion without significant ablation in one embodiment of the present invention. In a different embodiment of the present invention, generation laser beam 212 is absorbed and creates enough heat in the target surface to cause ablation that becomes the main mechanism of ultrasonic wave generation.

Illumination or detection laser 220 operating in pulsed mode or continuous wave mode does not induce ultrasonic displacements. For example, an Nd:YAG laser can be used. The power of this laser must be sufficient to deliver, for example, a 100 milli-joule, 100 micro-second pulse, which may require a one kilo-watt laser. Illumination laser 220 generates detection laser beam 224. Illumination laser 220 includes or optically couples to filtering mechanism 222 to remove noise from detection laser beam 224. Optical assembly 214 directs illumination laser beam 224 to the surface of composite material 216 which scatters and/or reflects detection laser beam 224. Resultant phase modulated light is collected by collection optics 226. As shown here, scattered and/or reflected illumination laser travels back through optical assembly 214. Optional optical processor 220 and interferometer 230 process the phase modulated light to produce a signal containing information representative of the ultrasonic displacements at the surface of composite material 216. Data processing and control system 232 coordinate operation of the laser ultrasound system components.

Data processing and control system 232 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may he a single memory device or a plurality of memory devices. Such a memory device may he a read-only memory, random access memory, volatile memory, non-volatile memory, static memory, dynamic memory, flash memory, cache memory, and/or any device that stores digital information. The memory stores, and data processing and control system 232 executes, operational instructions corresponding to at least some of the steps and/or functions as will be illustrated.

Figure 3:
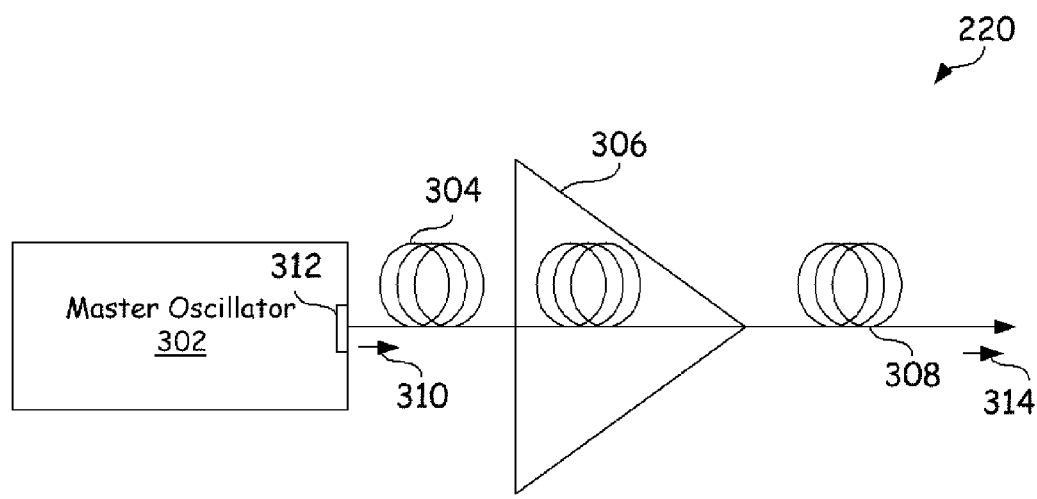
FIG. 3 illustrates the use of fiber laser as a detection laser beam to detect laser ultrasonic displacements in accordance with an embodiment of the present invention.

FIG. 3 depicts the use a fiber laser within a detection laser 220 in accordance with an embodiment of the present invention. The embodiment of the detection laser 220 depicted in FIG. 3 may use a master oscillator 302 that may be coupled to a single-mode pumped fiber amplifier 306 with optical fibers 304. Then the amplified laser beam may be delivered to the work piece or sample under test. The detection laser is applied to the materials to be inspected with optical fiber 308. Master oscillator 302 may be a diode pumped non-planar ring oscillator (NPRO) having a fiber-coupled output 312 that allows the generated seed detection laser beam 310 to he provided via a optical fiber 304 to diode pumped fiber amplifier 306. Another approach may construct an all fiber single-frequency laser using a fiber laser as the master oscillator 302 and one or more fiber lasers such as diode pumped fiber amplifier 306 as amplifiers as well.

Figure 4:
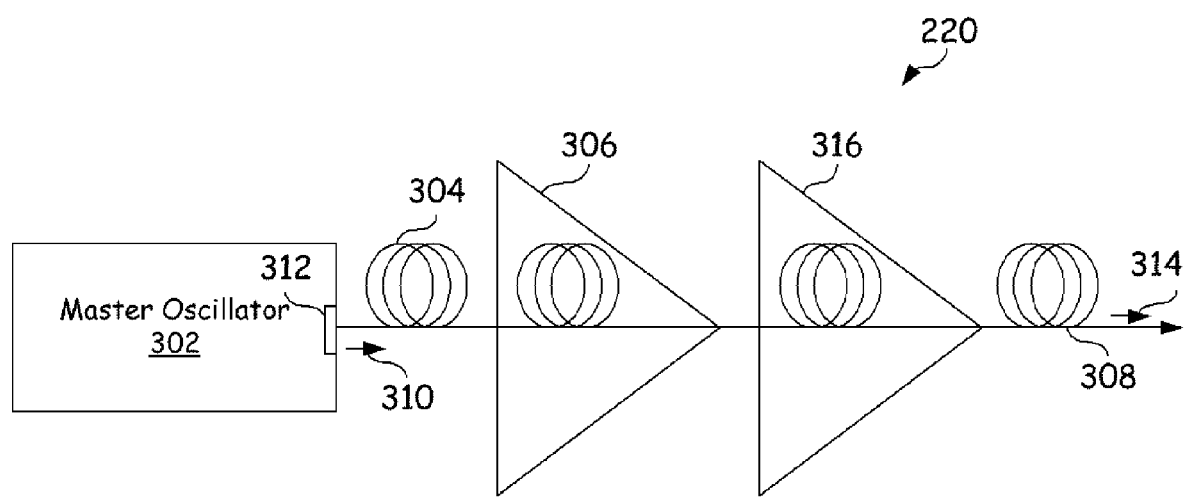
FIG. 4 illustrates the use of fiber laser as a detection laser beam to detect laser ultrasonic displacements in accordance with an embodiment of the present invention.

FIG. 4 depicts a second embodiment of detection laser 220 that uses a fiber laser in accordance with an embodiment of the present invention. In this case, master oscillator 302 is coupled to two or more diode pumped fiber amplifiers 306 and 316. As before, master oscillator 302 has a fiber coupled output 312 coupled to optical fiber 304. Master oscillator 302 generates seed laser 310 which is delivered to diode pumped pre-amplifier 306 via optical fiber 304. For purposes of example, the laser beam 310 produced by master oscillator 302, may be a 25 milli-watt laser. Diode pumped fiber preamplifier 306 may increase the power of laser beam 310 to 100 watts. If necessary, a second amplifier 316 may be used to further increase the power of the detection laser to 1,000 watts. The output of the fiber pumped amplifier 316 is then delivered to the materials to be tested using optical fiber 308.

Figure 5:
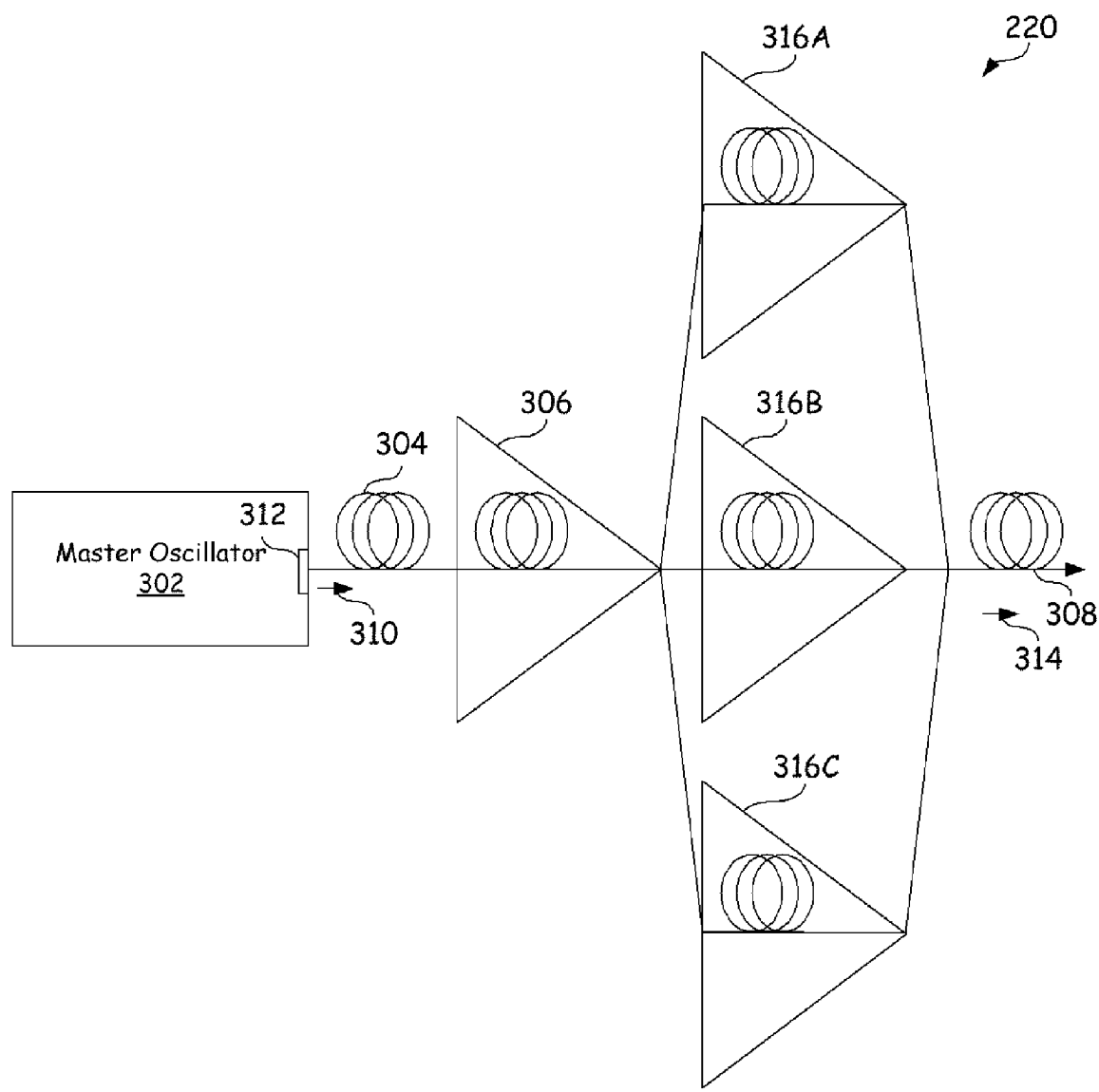
FIG. 5 illustrates the use of fiber laser as a detection laser beam to detect laser ultrasonic displacements in accordance with an embodiment of the present invention.
Figure 6:
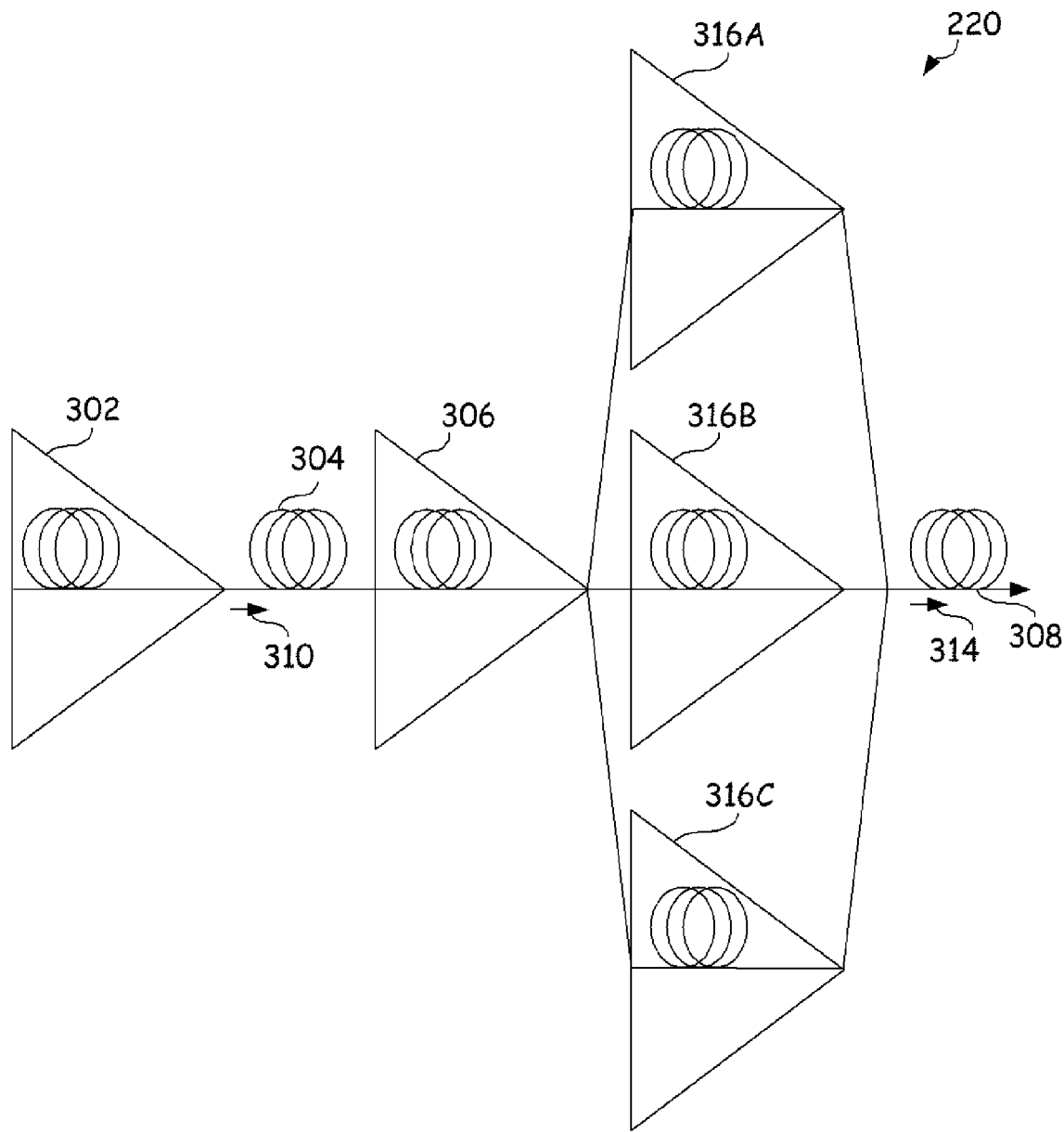
FIG. 6 illustrates the use of fiber laser as a detection laser beam to detect laser ultrasonic displacements in accordance with an embodiment of the present invention.

The level of power of single-frequency radiation produced by a single amplifier might be limited by a physical phenomenon called stimulated Brillouin scattering (SBS). When SBS occurs, the amplifier acts as a mirror, reflecting the radiation back towards the master oscillator, possibly damaging it and severely limiting the output power. In general, fiber 304 and amplifier fiber 306 are single-mode fibers with typical diameters smaller than 50 microns. The power threshold for which SBS occurs is proportional to the square of the fiber diameter. In order to produce single-frequency radiation at power levels exceeding the power threshold of SBS for the required fiber diameter of the fiber amplifier, several parallel fiber amplifiers can be used, each amplifier producing a power level below its own SBS threshold. The output single-mode fibers of all amplifiers are combined by fusion splice or by other technique into a larger multimode fiber that has a SBS threshold above the combined powers of the parallel amplifiers. FIGS. 5 and 6 present this approach as two embodiments of the present invention.

FIG. 5 depicts yet another embodiment of detection laser 220. As before this detection laser includes master oscillator 302, single-mode optical fiber 304, a first diode pumped fiber amplifier 306. The output optical fiber 308 is a large core diameter fiber, typically with a diameter larger than 50 microns, and the second stage has multiple parallel diode-pumped amplifiers 316A, 316B, and 316C. The output of these parallel diode pumped amplifiers may be combined within a single optical fiber. Master oscillator 302 produced a seed laser beam 310, which is provided via fiber coupled output 312 to optical fiber 304. In one embodiment of this example, the power output of master oscillator 302 may need to produce a laser beam 310 having a power of about 25 milli-watts. For illustrative purposes, diode pumped fiber preamplifier 306 may increase the power of this laser beam to approximately 100 watts. Then, the three parallel diode pumped fiber amplifiers 316A, 316B, and 316C are each coupled to the output of diode pumped fiber amplifier 306. Each diode pumped fiber amplifier produces a power below its own SBS threshold. The three parallel diode pumped fiber amplifiers 316A, 3162, and 316C may increase the power of the output laser beam 314 dramatically. As shown in this example, the multimode output may be greater than 1,000 watts when using this configuration of diode pumped fiber amplifiers.

FIG. 6 depicts yet another embodiment of detection laser 220 that uses a fiber laser in accordance with an embodiment of the present invention. In this embodiment, detection laser 220 again includes master oscillator 302, single-mode optical fiber 304, a first diode pumped fiber amplifier 306, a second series of diode pumped fiber amplifiers 316A, 3162, and 316C and a multi-mode output fiber optic 308 operable to deliver a detection laser beam 314. In this example, master oscillator 302 has been replaced with a diode pumped, single frequency fiber laser as opposed to NPRO.

The fiber laser associated with the master oscillator and the fiber amplifier may be: (1) Ytterbium doped fibers operable to produce radiation at a wavelength of about 1000 nm; or (2) Erbium doped or co-doped fibers operable to produce radiation at a wavelength of about 1550 nm. The fiber lasers may use side cladding pumping wherein pumping diodes are coupled to active fiber through pumping fibers. The pumping fibers couple to the active fiber through side cladding or an inner cladding of the active fiber. These pumping diodes may include single emitters, a group of single emitters, diode bars, and/or a group of diode bars.

Additionally, when multiple stages are used to amplify seed laser 310, some embodiments may employ a combination of diode pumped slab lasers and diode pumped fiber lasers. With all or part use of the use diode pumped fiber lasers to amplify or generate the detection laser offers many advantages. By using many small continuous wave (CW) diodes to pump the laser fiber, each fiber coupled pump diodes may be relatively small in power (typically only use a few watts). Therefore, the loss of any one or portion of the diodes may have little impact on the total performance of the laser to be generated.

The heat removal problems and thermal distortion of the wave profile of laser beam 314 is greatly reduced. The heat removal from the fiber-coupled diodes may be managed separately from the gain. In addition, these low power diodes typically offer greatly increased mean time between failure (MTBF) ratings that are currently available in slab in diode slab lasers. The thermal management of the fiber laser class amplifier is greatly improved when compared with the use of a traditional bulk crystal gain medium. This is the because the ratio of the fiber surface area (where the heat is removed from the fiber, to the volume where the laser is generated or amplified is many orders of magnitude larger than that of a bulk-surfaced volume ratio associated with a slab amplifier. Thus, the fiber laser may be operated in a single mode with very little wave front distortion. Since the fiber laser can be operated in a CW mode or a modulated-pulse mode, the speed limitation becomes not the laser speed but the ultrasound propagation time within the material to he tested and the scanning capabilities of other components used to scan the detection laser across the components to be tested. This allows effective scan rates to be 10 kHz, or higher. This offers a significant improvement when compared to scan rates of existing systems. Additionally, this flexible architecture may enable mobile and portable laser ultrasonic inspection system design suited for harsh industrial environments.

Figure 7:
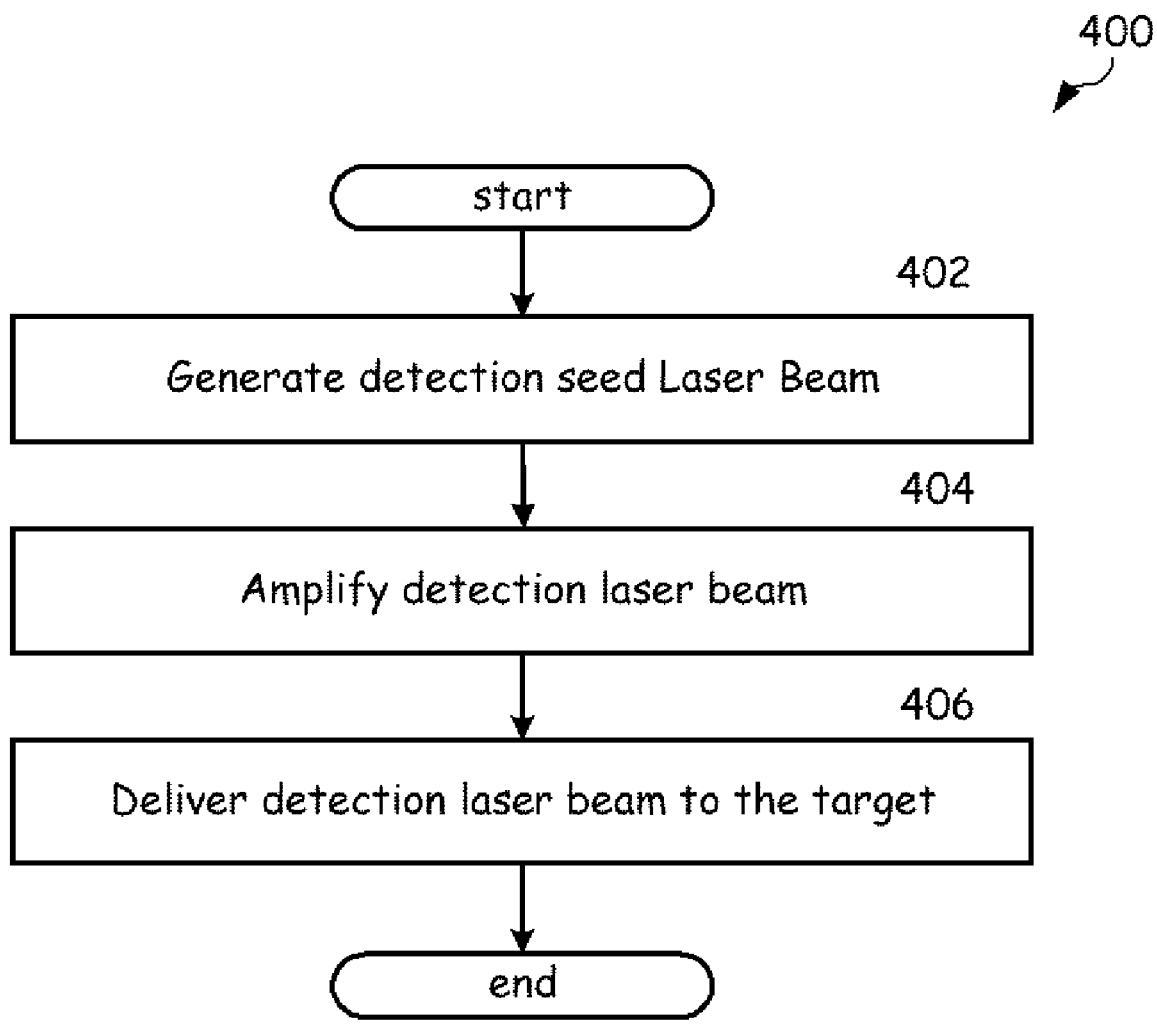
FIG. 7 provides a logic flow diagram in accordance with one or more embodiments for the present invention.

FIG. 7 provides a logic flow diagram in accordance with one or more embodiments for the present invention that depict how the detection laser may be generated within a laser ultrasound inspection system. Operations 400 began with the generation of a seed detection laser in Step 402. This seed detection laser beam may be a low power i.e. on the order of 25 milli-watt laser beam which may he amplified. This seed detection laser beam may be generated using a NPRO or a single pumped single frequency fiber laser or other means known to generate the seed detection laser. The seed laser beam may then he amplified using one or more diode pumped fiber amplifiers in step 404. In the embodiment previously depicted various combinations of diode pumped fiber laser amplifiers were employed to increase the power of the detection laser from 25 milli-watts to 1,000 or more watts. In step 406 the detection laser beam is delivered to the target.

In operation the present invention allows laser ultrasonic test equipment to be used in a wider range of environments while testing more complex surfaces or surfaces within limited access areas. The embodiments of the present invention may utilize fiber lasers to generate and deliver detection laser beams and possibly generation laser beams to a remote target to be tested. Doing so allows the overall size of a laser ultrasound system to he greatly reduced. For example, instead of a large gantry based system, a much smaller robotic system may he used to deliver generation and detection laser beams to the surface of the target to be tested. This allows the laser ultrasound inspection system offered by embodiments of the present invention to he used to not only inspect individual components hut to assess the internal structure of integrated components. Thus, not only can individual parts he inspected by the laser ultrasound system offered by embodiments of the present invention hut assembled structures made of individual parts may he inspected. This allows inspections to he made after the integrated structure has been built to see if there are any changes in the internal structure over the life of the structure. Additionally embodiments of the present invention may provide an entirely mobile system that uses fiber lasers to detect ultrasonic displacements at a remote target in the field without the problems often associated with free space delivery of detection of a detection laser beam.

Fiber lasers can produce laser emission at wavelengths similar or identical to the 1064-nm wavelength currently used for industrial laser-ultrasonic inspection by using Ytterbium doped fibers. Ytterbium-doped fibers can therefore replace currently-used diode-pumped or flash-pumped rod or slab detection lasers without the necessity to replace any of the optics and detectors. However, Erbium-doped or Erbium-co doped fibers can produce laser emission at wavelengths around 1550 nm. This wavelength range is commonly qualified as eye-safe. Safety requirements are significantly reduced when using an eye-safe wavelength in comparison to wavelengths around 1000 nm. Those reduced safety requirements could translate in important reduction in capital and operating costs if a laser-ultrasound inspection system were to be used in an open field or in a manufacturing environment.

An additional advantage of using a detection laser operating in a wavelength around 1550 nm is the possibility to leverage the huge quantity of optical technologies like detectors, modulators, optical fibers, etc. developed for telecommunication.

Fiber lasers and fiber amplifiers can be pumped using different approaches. The most popular approach is cladding-pumping where the pumping radiation is inserted in the cladding of the fiber laser or amplifier. Cladding pumping can be done either from the cladding end (end pumping) or the cladding side (side-pumping). Side-pumping eliminates the difficulties of end or coaxial pumping, where off-axis core designs or twisted active and pump fiber designs. In addition, a fused-fiber coupling eliminates the need for focusing optics and alignment, and is more robust than other designs such as end or V-groove pumping By employing individual diodes and a cladding side-pumping technology, the power can he scaled up by the introduction of additional pump diodes with no adverse effect on reliability. The lifetime of the individual diodes is orders of magnitude larger that of diode bars. Additionally, single emitters are independent from each other and when one emitter fails, contrarily to diode bars it does not affect any other emitter. Finally, in case of the failure of a single emitter, the decrease in total output power of the fiber laser or amplifier is very small because of the large number of diode emitters.

In summary, embodiments of the present invention relates to an improved laser for the optical detection of ultrasound. The primary task of this "first" detection laser is to illuminate the spot where a "second" laser is used to generate ultrasound in the part under test. The scattered light from the first laser is collected and analyzed with an interferometer to demodulate the surface vibrations caused by the return echoes of the ultrasound at the surface of the part. The improved detection laser (first laser) is constructed using a diode-pumped fiber laser to produce a high power single-frequency laser source.

As one of average skill in the art will appreciate, the term "substantially" or "approximately", as may be used herein, provides an industry-accepted tolerance to its corresponding term. Such an industry-accepted tolerance ranges from less than one percent to twenty percent end corresponds to, hut is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A method to detect ultrasonic surface displacements at a remote target comprising:
    generating ultrasonic displacements at a surface of the remote target;
    providing a diode pumped detection fiber laser comprising:
        a master oscillator comprising a diode pumped fiber laser;
        a diode pumped laser pre-amplifier comprising a diode pumped fiber laser amplifier; and
        a diode pumped laser amplifier comprising a diode pumped fiber laser amplifier;
    generating a seed laser beam using the master oscillator;
    amplifying the seed laser beam to generate an output laser beam using the diode pumped laser pre-amplifier;
    amplifying the output laser beam using the diode pumped laser amplifier to thereby generate a detection laser beam;
    directing the detection laser beam to the surface of the remote target;
    scattering the detection laser beam with the ultrasonic surface displacements at the surface to produce phase modulated light;
    collecting the phase modulated light;
    processing the phase modulated light to obtain data representative of the ultrasonic surface displacements at the surface; and
    collecting the data with the information to analyze structures within the remote target.

2. The method of claim 1, wherein generating ultrasonic displacements at a surface of the remote target further comprises:
    directing a generation laser beam to illuminate a portion of a surface of the remote target, wherein the ultrasonic surface displacements occur within the illuminated portion of the surface of the remote target.

3. The method of claim 1, further comprising processing the data to assess the structural integrity of the remote target.

4. The method of claim 1, wherein the master oscillator or the at least one diode pumped laser amplifier comprises a diode pumped slab laser.

5. The method of claim 1, wherein the master oscillator and/or the at least one diode pumped laser amplifier comprise Ytterbium doped fibers operable to produce radiation at a wavelength of about 1000 nm.

6. The method of claim 1, wherein the master oscillator and/or the at least one diode pumped laser amplifier comprise Erbium doped or co-doped fibers operable to produce radiation at a wavelength of about 1550 nm.

7. The method of claim 1, wherein the master oscillator and/or the at least one diode pumped laser amplifier comprise fiber lasers having side cladding pumping wherein pumping diodes are coupled to active fiber through pumping fibers.

8. The method of claim 7, wherein the pumping fibers couple to the active fiber through side cladding or an inner cladding of the active fiber.

9. The method of claim 7, wherein the pumping diodes comprise single emitters a group of single emitters diode bars, and/or a group of diode bars.

10. An apparatus operable to detect ultrasonic surface displacements on a remote target comprising:
   an ultrasound generation system operable to produce ultrasonic surface displacements at the remote target;
   a diode pumped detection fiber laser operable to generate a detection laser beam that substantially illuminates the ultrasonic surface displacements at the remote target;
   collection optics operable to collect phase modulated light from the diode pumped detection fiber laser either reflected or scattered by the remote target; and
   a processor operable to: process the phase modulated light from the diode pumped detection fiber laser either reflected or scattered by the remote target to obtain data representative of the ultrasonic displacements at the remote target; and
      process the data representative of the ultrasonic displacements to assess the structural integrity of the remote target;
   wherein the diode pumped detection fiber laser comprises:
      a master oscillator operable to generate a seed laser beam, wherein the master oscillator comprises a diode pumped fiber laser;
      at least one diode pumped laser pre-amplifier operable to amplify the seed laser beam, wherein the at least one diode pumped laser pre-amplifier comprises a diode pumped fiber laser amplifier; and
      at least one diode pumped laser amplifier operable to amplify an output laser beam produced by the at least one diode pumped laser pre-amplifier, wherein the at least one diode pumped laser amplifier comprises a diode pumped fiber laser amplifier.

11. The apparatus of claim 10, wherein the ultrasound generation system is operable to:
   direct a generation laser beam to illuminate a portion of a surface of the remote target, wherein the ultrasonic surface displacements occur within the illuminated portion of the surface of the remote target.

12. The apparatus of claim 10, wherein the master oscillator and/or the at least one diode pumped laser amplifier comprise Ytterbium doped fibers operable to produce a radiation at a wavelength around 1000 nm.

13. The apparatus of claim 10, wherein the master oscillator and/or the at least one diode pumped laser amplifier comprise Erbium doped or co-doped fibers operable to produce radiation at a wavelength of about 1550 nm.

14. The apparatus of claim 10, wherein the master oscillator and/or the at least one diode pumped laser amplifier comprise fiber lasers having side cladding pumping wherein pumping diodes are coupled to active fiber through pumping fibers.

15. The apparatus of claim 14, wherein the pumping fibers couple to the active fiber through side cladding or an inner cladding of the active fiber.

16. The apparatus of claim 14, wherein the pumping diodes comprise single emitters a group of single emitters diode bars, and/or a group of diode bars.

17. The apparatus of claim 10, wherein diode pumped detection fiber laser comprises:
   at least two parallel diode pumped laser amplifiers operable to amplify the seed laser beam, wherein the at least two parallel diode pumped laser amplifiers comprise diode pumped fiber laser, wherein an output of the at least two parallel diode pumped laser amplifiers are combined within a single optical fiber.

18. The apparatus of claim 10, wherein the master oscillator or the at least one diode pumped laser amplifier comprises a diode pumped slab laser.

* * * * *

UNITED STATES PATENT AND TRADEMARK OFFICE
CERTIFICATE OF CORRECTION

PATENT NO. : 7,612,894 B2 Page 1 of 1
APPLICATION NO. : 11/458377
DATED : November 3, 2009
INVENTOR(S) : Drake et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this

Nineteenth Day of October, 2010

David J. Kappos
*Director of the United States Patent and Trademark Office*